United States Patent
Kramer et al.

(10) Patent No.: US 7,077,853 B2
(45) Date of Patent: Jul. 18, 2006

(54) METHOD FOR CALCULATING TRANSDUCER CAPACITANCE TO DETERMINE TRANSDUCER TEMPERATURE

(75) Inventors: Kenneth S. Kramer, Loveland, OH (US); Eitan T. Wiener, Cincinnati, OH (US); William T. Donofrio, Cincinnati, OH (US); Kevin Houser, Springboro, OH (US); Foster B. Stulen, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 491 days.

(21) Appl. No.: 09/975,390

(22) Filed: Oct. 10, 2001

(65) Prior Publication Data
US 2002/0062132 A1 May 23, 2002

Related U.S. Application Data

(60) Provisional application No. 60/241,891, filed on Oct. 20, 2000.

(51) Int. Cl.
*A61B 17/32* (2006.01)
(52) U.S. Cl. .................................. 606/169; 702/75
(58) Field of Classification Search .............. 606/169, 606/166, 127, 167, 170, 179, 171, 180, 32, 606/39, 41, 42; 600/1, 437, 438, 439, 463; 324/519; 128/898; 604/22
See application file for complete search history.

(56) References Cited

U.S. PATENT DOCUMENTS

| | | | |
|---|---|---|---|
| 2,917,691 A | 12/1959 | DePrisco et al. ........... 318/118 |
| 3,608,553 A * | 9/1971 | Balamuth ................. 606/131 |
| 3,781,717 A * | 12/1973 | Kuenemund ............... 333/133 |
| 4,689,515 A * | 8/1987 | Benndorf et al. ........ 310/316.01 |
| 5,001,649 A | 3/1991 | Lo et al. .................... 364/484 |
| 5,026,387 A | 6/1991 | Thomas ..................... 606/169 |
| 5,112,300 A | 5/1992 | Ureche ....................... 604/22 |
| 5,180,363 A | 1/1993 | Idemoto et al. ............. 202/32 |
| 5,400,267 A | 3/1995 | Denen et al. ............... 364/552 |
| 5,425,704 A | 6/1995 | Sakurai et al. .............. 604/22 |
| 5,449,370 A | 9/1995 | Vaitekunas ................. 606/169 |
| 5,630,420 A | 5/1997 | Vaitekunas ............. 128/662.03 |
| 5,707,369 A | 1/1998 | Vaitekunas et al. .......... 606/31 |
| 5,735,280 A * | 4/1998 | Sherman et al. ............. 600/1 |
| 5,879,364 A | 3/1999 | Bromfield et al. ........ 606/169 |
| 5,968,007 A | 10/1999 | Simon et al. ................ 604/22 |
| 6,017,354 A | 1/2000 | Culp et al. ................. 606/170 |
| 6,019,775 A | 2/2000 | Sakurai ..................... 606/169 |

(Continued)

FOREIGN PATENT DOCUMENTS

JP 2000-175926 6/2000

*Primary Examiner*—Julian W. Woo
*Assistant Examiner*—Victor X. Nguyen
(74) *Attorney, Agent, or Firm*—Verne E. Kreger, Jr.

(57) ABSTRACT

A method for calculating the capacitance of a transducer ($C_0$) without knowing the exact resonance frequency of a transducer/blade combination is achieved by sweeping across a broad frequency range which contains resonant and non-resonant frequencies where $C_0$ can be measured. A pre-defined frequency range is set independently of the resonance frequency of a specific transducer/blade combination. $C_0$ of the transducer/blade is measured at several different frequencies within the pre-defined frequency range to ensure that invalid $C_0$ measurements are disregarded, and the temperature of the transducer is calculated based on valid $C_0$ measurements. The determined transducer temperature, based on $C_0$ measurements, can be used to optimize performance and/or provide a safety shutdown mechanism for the generator.

12 Claims, 11 Drawing Sheets

U.S. PATENT DOCUMENTS

| | | | |
|---|---|---|---|
| 6,066,135 A | 5/2000 | Honda | 606/39 |
| 6,090,123 A | 7/2000 | Culp et al. | 606/180 |
| 6,454,781 B1 * | 9/2002 | Witt et al. | 606/169 |
| 6,626,926 B1 * | 9/2003 | Friedman et al. | 606/169 |
| 6,655,386 B1 * | 12/2003 | Makower et al. | 128/898 |
| 6,679,899 B1 * | 1/2004 | Wiener et al. | 606/169 |

* cited by examiner

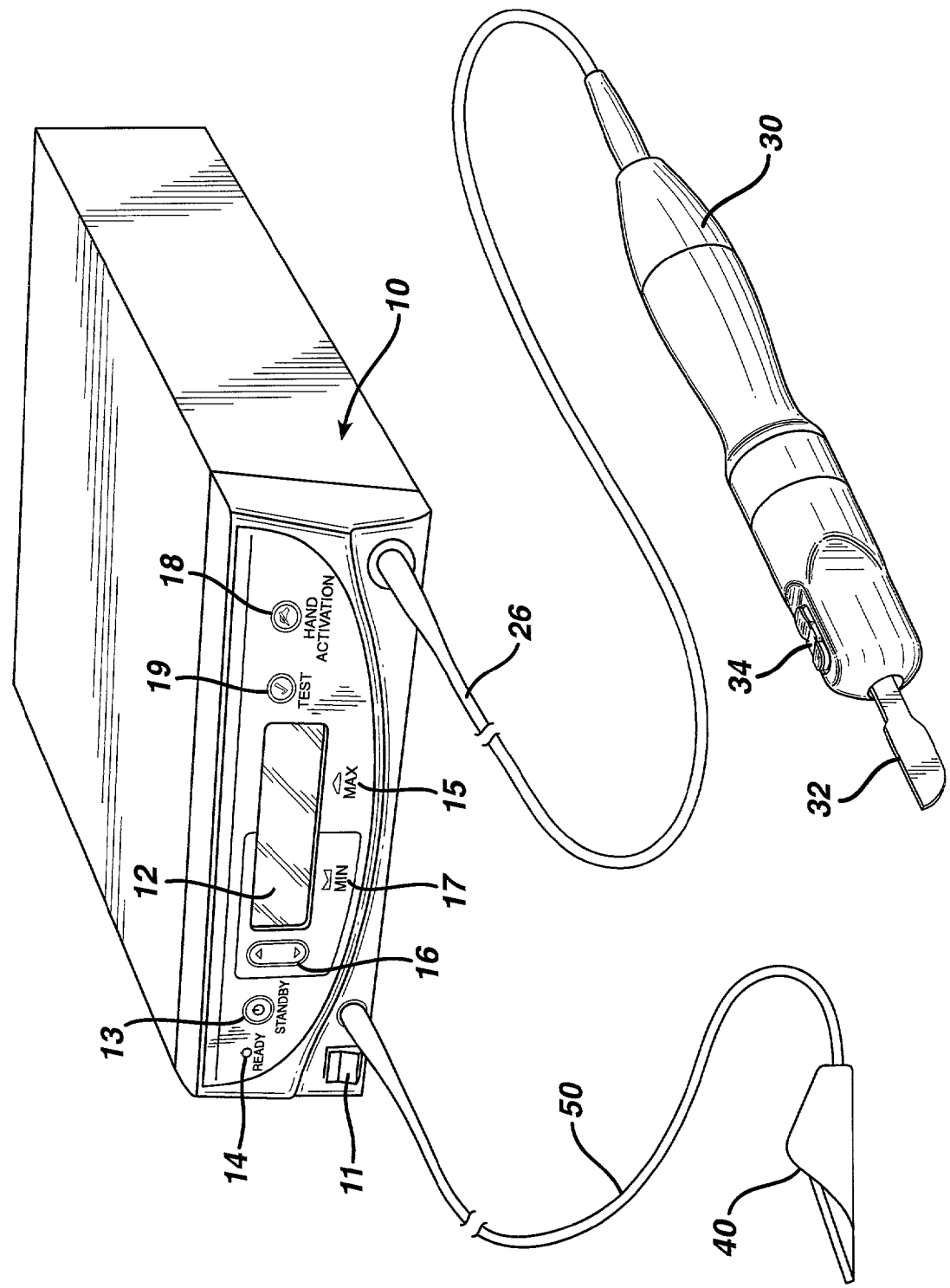

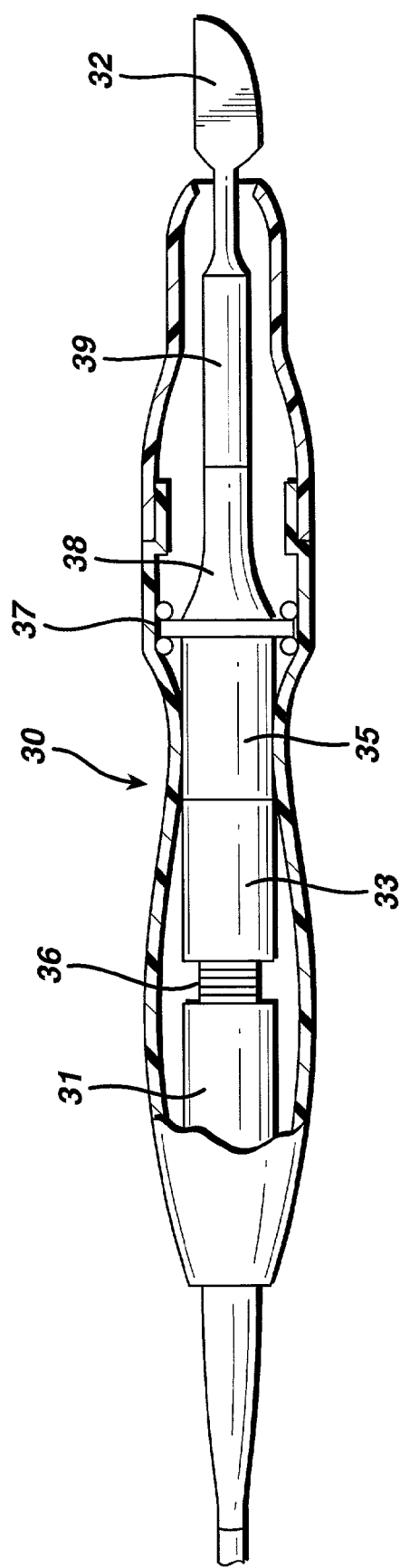

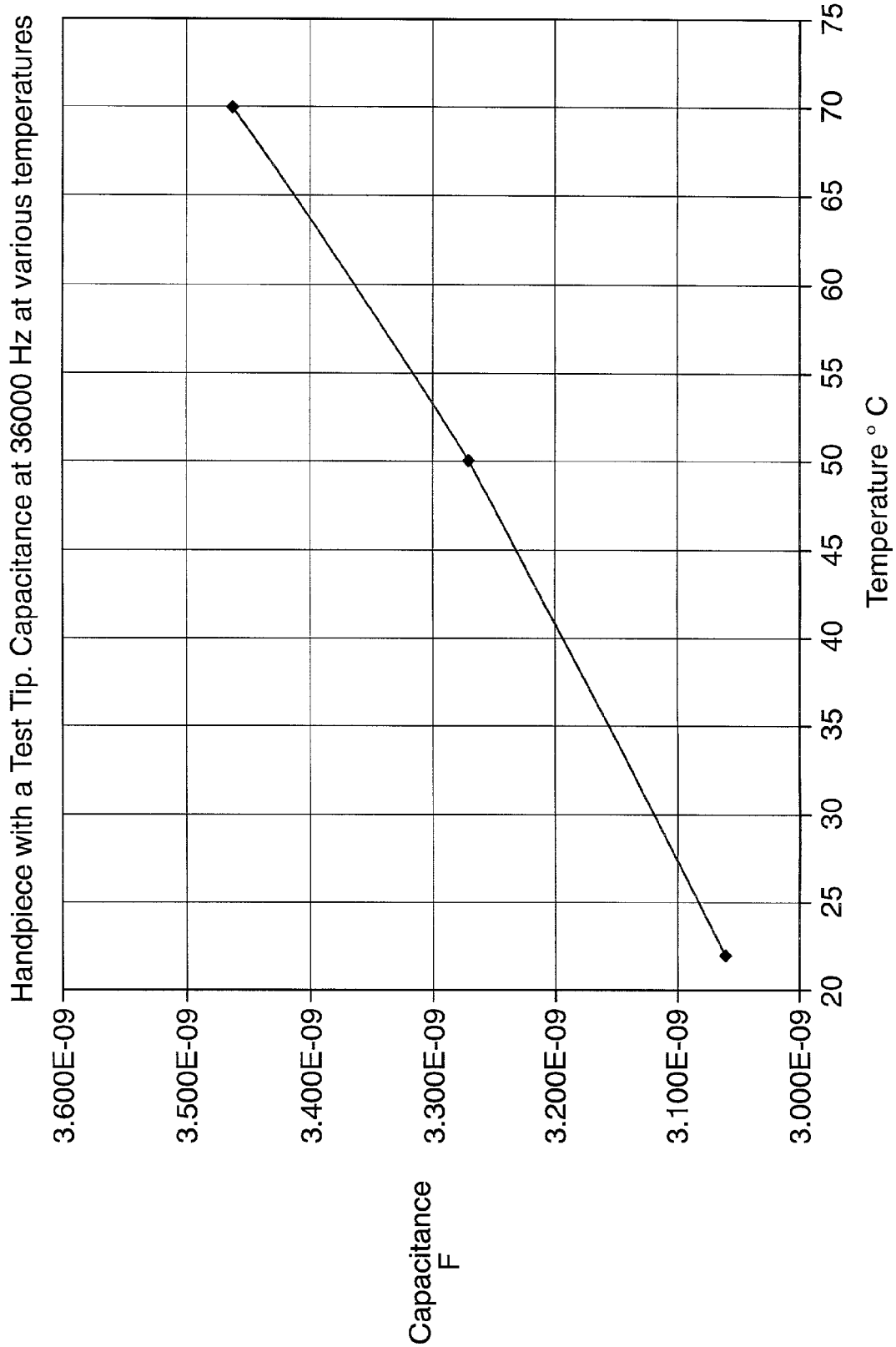

METHOD FOR CALCULATING TRANSDUCER CAPACITANCE TO DETERMINE TRANSDUCER TEMPERATURE

RELATED APPLICATIONS

The present invention relates to, and claims priority of, U.S. Provisional Patent Application Ser. No. 60/241,891 filed on Oct. 20, 2000, having the same title as the present invention, which is incorporated herein by reference.

BACKGROUND OF THE INVENTION

1. Field of the Invention

The present invention generally relates to ultrasonic surgical systems and, more particularly, to a method for determining the temperature of an ultrasonic transducer.

2. Description of the Related Art

It is known that electric scalpels and lasers can be used as a surgical instrument to perform the dual function of simultaneously effecting the incision and hemostatis of soft tissue by cauterizing tissues and blood vessels. However, such instruments employ very high temperatures to achieve coagulation, causing vaporization and fumes as well as splattering. Additionally, the use of such instruments often results in relatively wide zones of thermal tissue damage.

Cutting and cauterizing of tissue by means of surgical blades vibrated at high speeds by ultrasonic drive mechanisms is also well known. One of the problems associated with such ultrasonic cutting instruments is uncontrolled or undamped vibrations and the heat, as well as material fatigue resulting therefrom. In an operating room environment attempts have been made to control this heating problem by the inclusion of cooling systems with heat exchangers to cool the blade. In one known system, for example, the ultrasonic cutting and tissue fragmentation system requires a cooling system augmented with a water circulating jacket and means for irrigation and aspiration of the cutting site. Another known system requires the delivery of cryogenic fluids to the cutting blade.

It is known to limit the current delivered to the transducer as a means for limiting the heat generated therein. However, this could result in insufficient power to the blade at a time when it is needed for the most effective treatment of the patient. U.S. Pat. No. 5,026,387 to Thomas, which is assigned to the assignee of the present application and is incorporated herein by reference, discloses a system for controlling the heat in an ultrasonic surgical cutting and hemostasis system without the use of a coolant, by controlling the drive energy supplied to the blade. In the system according to this patent an ultrasonic generator is provided which produces an electrical signal of a particular voltage, current and frequency, e.g. 55,500 cycles per second. The generator is connected by a cable to a hand piece which contains piezoceramic elements forming an ultrasonic transducer. In response to a switch on the hand piece or a foot switch connected to the generator by another cable, the generator signal is applied to the transducer, which causes a longitudinal vibration of its elements. A structure connects the transducer to a surgical blade, which is thus vibrated at ultrasonic frequencies when the generator signal is applied to the transducer. The structure is designed to resonate at the selected frequency, thus amplifying the motion initiated by the transducer.

The signal provided to the transducer is controlled so as to provide power on demand to the transducer in response to the continuous or periodic sensing of the loading condition (tissue contact or withdrawal) of the blade. As a result, the device goes from a low power, idle state to a selectable high power, cutting state automatically depending on whether the scalpel is or is not in contact with tissue. A third, high power coagulation mode is manually selectable with automatic return to an idle power level when the blade is not in contact with tissue. Since the ultrasonic power is not continuously supplied to the blade, it generates less ambient heat, but imparts sufficient energy to the tissue for incisions and cauterization when necessary.

The control system in the Thomas patent is of the analog type. A phase lock loop (that includes a voltage controlled oscillator, a frequency divider, a power switch, a matching network and a phase detector), stabilizes the frequency applied to the hand piece. A microprocessor controls the amount of power by sampling the frequency, current and voltage applied to the hand piece, because these parameters change with load on the blade.

The power versus load curve in a generator in a typical ultrasonic surgical system, such as that described in the Thomas patent, has two segments. The first segment has a positive slope of increasing power as the load increases, which indicates constant current delivery. The second segment has a negative slope of decreasing power as the load increases, which indicates a constant or saturated output voltage. The regulated current for the first segment is fixed by the design of the electronic components and the second segment voltage is limited by the maximum output voltage of the design. This arrangement is inflexible since the power versus load characteristics of the output of such a system can not be optimized to various types of hand piece transducers and ultrasonic blades. The performance of traditional analog ultrasonic power systems for surgical instruments is affected by the component tolerances and their variability in the generator electronics due to changes in operating temperature. In particular, temperature changes can cause wide variations in key system parameters such as frequency lock range, drive signal level, and other system performance measures.

In order to operate an ultrasonic surgical system in an efficient manner, during startup the frequency of the signal supplied to the hand piece transducer is swept over a range to locate the resonance frequency. Once it is found, the generator phase lock loop locks on to the resonance frequency, continues to monitor the transducer current to voltage phase angle, and maintains the transducer resonating by driving it at the resonance frequency. A key function of such systems is to maintain the transducer resonating across load and temperature changes that vary the resonance frequency. However, these traditional ultrasonic drive systems have little to no flexibility with regards to adaptive frequency control. Such flexibility is key to the system's ability to discriminate undesired resonances. In particular, these systems can only search for resonance in one direction, i.e., with increasing or decreasing frequencies and their search pattern is fixed. The system cannot: (i) hop over other resonance modes or make any heuristic decisions, such as what resonance to skip or lock onto, and (ii) ensure delivery of power only when appropriate frequency lock is achieved.

The prior art ultrasonic generator systems also have little flexibility with regard to amplitude control, which would allow the system to employ adaptive control algorithms and decision making. For example, these fixed systems lack the ability to make heuristic decisions with regards to the output drive, e.g., current or frequency, based on the load on the blade and/or the current to voltage phase angle. It also limits the system's ability to set optimal transducer drive signal levels for consistent efficient performance, which would increase the useful life of the transducer and ensure safe operating conditions for the blade. Further, the lack of control over amplitude and frequency control reduces the system's ability to perform diagnostic tests on the transducer/blade system and to support troubleshooting in general.

Some limited diagnostic tests performed in the past involve sending a signal to the transducer to cause the blade to move and the system to be brought into resonance or some other vibration mode. The response of the blade is then determined by measuring the electrical signal supplied to the transducer when the system is in one of these modes. The ultrasonic system described in U.S. application Ser. No. 09/693,621, filed on Oct. 20, 2000, which is incorporated herein by reference, possesses the ability to sweep the output drive frequency, monitor the frequency response of the ultrasonic transducer and blade, extract parameters from this response, and use these parameters for system diagnostics. This frequency sweep and response measurement mode is achieved via a digital code such that the output drive frequency can be stepped with high resolution, accuracy, and repeatability not existent in prior art ultrasonic systems.

When using ultrasonic surgical generators, access to the transducer temperature is of particular importance. The temperature of the transducer can be used to optimize the overall performance of the ultrasonic surgical system, as well as to enhance the overall safety of the system during use, such as to determine whether it is safe to handle or grab the hand piece. For example, during use of the ultrasonic surgical system, such as while performing surgery, the impedance of the transducer can increase such that electrical losses within the transducer increase which can lead to excessive hand piece temperatures. It is therefore advantageous to know the temperature of the transducer to prevent undesired effects, such as injury to an operator as a result of grabbing a hot hand piece, or to prevent injury to a patient as a result of exposure to bare hand piece surfaces.

Measuring the temperature of the transducer is relatively simple. Traditionally, thermocouples, thermistors and other classical temperature sensors are used to measure the transducer temperature for control and safety purposes. However, these methods increase the cost of the hand piece, and add additional wires and connections which could potentially reduce the reliability of the ultrasonic surgical system.

SUMMARY OF THE INVENTION

The present invention provides a method of determining the transducer temperature by measuring the shunt capacitance of the transducer ($C_O$), and using the shunt capacitance to calculate the transducer temperature.

A transducer with or without a blade will always possess non-resonant frequencies at which $C_O$ of the transducer can be measured. However, the particular non-resonant frequencies will vary depending on which blade is attached and the type of transducer in use. Given a known non-resonant frequency of a blade, the measurement of $C_O$ is relatively simple and fast to perform. However, if the resonant frequencies of the blade must first be identified and $C_O$ then measured at non-resonant frequencies, a considerable amount of time and effort will be consumed. In such a case, the determination of $C_O$ is difficult, because the frequency at which $C_O$ is measured preferably resides at a non-resonant frequency. Typically, the particular non-resonant frequencies used to measure $C_O$ are almost always present in the blade. However, if the design of the blade is changed, the detection of these particular non-resonant frequencies is not assured. Accordingly, the invention ensures isolation of $C_O$ from resonances or a nearby resonance to determine the transducer/blade temperature.

The invention therefore comprises a method for calculating the capacitance of a transducer ($C_O$) without knowing the exact resonance frequency of a transducer/blade combination. The invention also comprises a method for determining the temperature of the transducer without the use of a temperature sensor, or the like. The method of the invention is achieved by sweeping across a broad frequency range which contains resonant and non-resonant frequencies where $C_O$ can be measured. A pre-defined frequency range is set independently of the resonance frequency of a specific transducer/blade combination. $C_O$ of the transducer/blade is measured at several different frequencies within the pre-defined frequency range to ensure that invalid $C_O$ measurements are disregarded, and the temperature of the transducer is calculated based on valid $C_O$ measurements.

The method according to the invention is adaptive, in that $C_O$ is identified independently of any variances of the resonance frequencies of the blade which may occur. In this manner, the method provides greater design freedom for future transducer and blade designs, since the location of a "quiet" non-resonant zone within a specific frequency range is not required. By using selective averaging of $C_O$ and measurements at different frequencies, the present invention achieves $C_O$ measurements which are more accurate than those obtained by a single $C_O$ measurement. Moreover, by eliminating $C_O$ measurements which appear disrupted by resonances at specific frequencies and by focusing only on distinct potentially valid $C_O$ values, a rapid calculation and an accurate identification of the shunt capacitance is achieved. In accordance with the invention, during manufacture of the hand piece, the measured capacitance at an off-resonance frequency (i.e., $C_O$ at a frequency other than resonance) is stored in non-volatile memory located in the hand piece (i.e., in an integrated circuit memory inside the connector, cable or body of the hand piece).

In an embodiment of the invention, the hand piece is measured to determine its impedance $Z_{HP}$. A comparison is made to determine whether the phase of the hand piece is within acceptable limits. If the absolute value of the phase of the hand piece is less than a predetermined value, then the drive frequency level is incremented by a fixed amount. If, on the other hand, the absolute value of the phase of the hand piece is greater than the predetermined value, then $Z_{HP}$ of the hand piece is measured a number of times.

An average $C_O$ value is computed at each generator drive frequency level for each non-resonant frequency. The drive frequency is incremented, and a check is made to determined whether the drive frequency is greater than a maximum frequency or whether the total number of $Z_{HP}$ measurements is greater than a predetermined number. If either of these conditions are met, then the average value of the $C_O$ values measured at each drive frequency is computed. If, on the other hand, the drive frequency is less than the maximum frequency or the total number of $Z_{HP}$ measurements is less than the predetermined number then additional $C_O$ values are determined. In the preferred embodiment, the maximum frequency is 44.5 kHz.

To determine whether the transducer temperature is within acceptable limits, a calculation is performed to determine a calculated value for $C_O$. The calculated value is compared to a $C_O$ value stored in non-volatile memory during manufacture of the hand piece. If the calculated value for $C_0$ is greater than a predetermined threshold above the $C_0$ value stored in non-volatile memory, then the transducer temperature is excessive and a warning is provided to the user. In the preferred embodiment, power to the hand piece is removed until such time as the shunt capacitance falls below the predetermined threshold.

In the preferred embodiment of the invention, the hand piece is measured at fixed frequency intervals to determine its impedance $Z_{HP}$ at each frequency interval. Using the data points obtained during the impedance measurement, a curve fit is then performed to obtain a curve fit equation.

This equation is solved at a number of equally spaced frequency values to arrive at a group of distinct impedance values. The shunt capacitance is calculated for each of the distinct impedance values. The maximum calculated capacitance value and the minimum calculated shunt capacitance value is discarded. An average of the remaining values is then calculated to thereby "smooth" the high and low values, and arrive at a final shunt capacitance value.

If the shunt capacitance is greater than a predetermined threshold based on a $C_0$/Temp relationship, then the transducer temperature is excessive and a warning is provided to the user. Alternatively, power to the hand piece is removed until such time as the shunt capacitance falls below the predetermined threshold. In the preferred embodiment, the predetermined threshold is a fixed amount above the capacitance of the hand piece/blade at room temperature, and the fixed amount is 462 pF.

In another embodiment of the invention, the rate of change of the measured shunt capacitance ($C_0$) of the transducer is measured and compared to a predetermined threshold. If the rate of change is greater than the predetermined threshold, the transducer/blade is on the verge of over heating, or will do so in the near future. The $C_0$ of the transducer is measured when a surgeon first activates the hand piece using the foot switch of the ultrasonic generator or the switch on the hand piece. A second measurement is performed upon release of either switch by the surgeon. The difference between the two measurements is calculated and divided by a time difference to arrive at a value which is representative of the rate of change of the capacitance. Here, the time difference is the time between the surgeon activating and releasing the foot switch. If the rate of change value for the shunt capacitance exceeds a predetermined threshold stored in memory, a warning is provided to the surgeon before the temperature of the transducer becomes excessive, and therefore presents a danger of injury to the surgeon or patient.

In a further embodiment of the invention, the temperature of the transducer is determined without the use of temperature sensors. This is accomplished by using non-volatile memory which is embedded in the hand piece to enhance the overall performance and safety of the system. The measured capacitance at an off-resonance frequency (i.e., the shunt capacitance ($C_0$) at a frequency other than resonance) is stored in the non-volatile memory. Linear regression analysis of the values of the transducer capacitance, as it changes with temperature and hand piece use, is also stored in non-volatile memory in the generator.

Prior to and/or during hand piece activation, the generator performs a "read" of the room temperature capacitance data from the hand piece. The actual capacitance of the hand piece is then measured in accordance with the invention, and the actual transducer temperature is calculated using a polynomial curve stored in the non-volatile memory of the generator. The temperature data is then used to determined whether it is safe to activate the hand piece, as well as to determine what levels of parameters to expect during diagnostic measurements. In this manner, a means to indirectly measure the temperature of the transducer is achieved. In addition, the need for temperature sensors, wires and connector pins for performing temperature measurements are eliminated.

Using the method of the invention, greater design freedom for future transducer and blade designs is achieved, since the location of a "quiet" non-resonant zone within a specific frequency range is not required. By eliminating the need to measure resonance frequencies, the invention greatly increases and enhances the speed at which $C_0$ is determined. By using selective averaging of $C_0$ and measurements at different frequencies, the present invention achieves $C_0$ measurements which are more accurate than those obtained by a single $C_0$ measurement. By eliminating $C_0$ measurements which appear disrupted by resonances at specific frequencies and by focusing only on distinct potentially valid $C_0$ values, a rapid calculation and an accurate identification of the shunt capacitance is achieved. Moreover, the "sampling process" is improved due to the avoidance of resonances and/or resonance zones which are located adjacent to frequencies at which $C_0$ measurements are performed. In addition the method provides indirect measurement of the temperature of the transducer, and the need for temperature sensors, wires and connector pins for performing temperature measurements are eliminated.

BRIEF DESCRIPTION OF THE DRAWINGS

The foregoing and other advantages and features of the invention will become more apparent from the detailed description of the preferred embodiments of the invention given below with reference to the accompanying drawings in which:

FIG. 1 is an illustration of a console for an ultrasonic surgical cutting and hemostasis system, as well as a hand piece and foot switch in which the method of the present invention is implemented;

FIG. 2 is a schematic view of a cross section through the ultrasonic scalpel hand piece of the system of FIG. 1;

FIG. 9 is a graph of capacitance vs. temperature for a hand piece fitted with a test tip.

DETAILED DESCRIPTION OF THE PREFERRED EMBODIMENTS

Figure 3A:
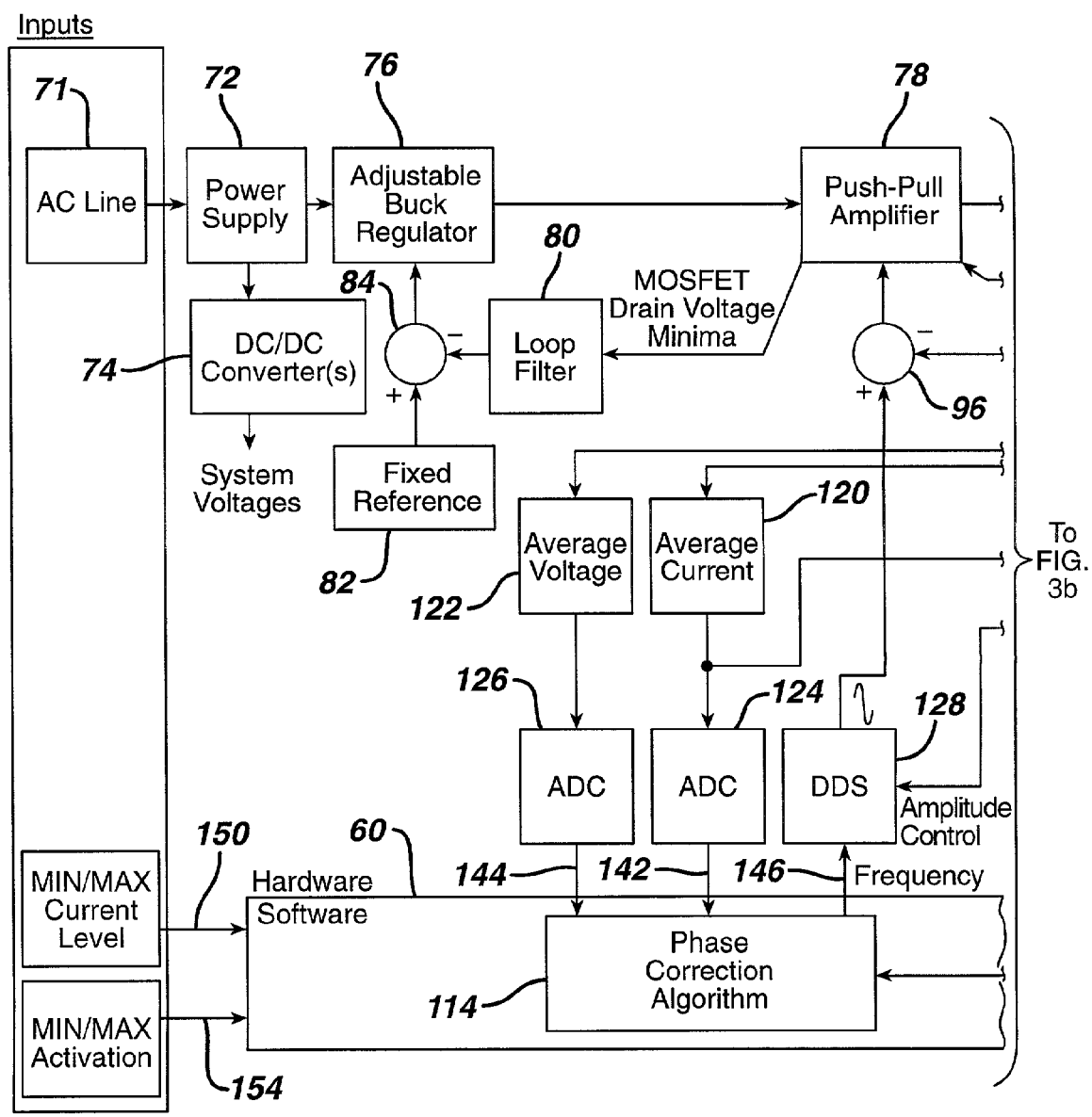
FIGS. 3(a) and 3(b) are block diagrams illustrating an ultrasonic generator for implementing the method of the invention.

FIG. 1 is an illustration of a system for implementing the method in accordance with the invention. By means of a first set of wires in cable 26, electrical energy, i.e., drive current, is sent from the console 10 to a hand piece 30 where it imparts ultrasonic longitudinal movement to a surgical device, such as a sharp scalpel blade 32. This blade can be used for simultaneous dissection and cauterization of tissue.

The supply of ultrasonic current to the hand piece 30 may be under the control of a switch 34 located on the hand piece, which is connected to the generator in console 10 via wires in cable 26. The generator may also be controlled by a foot switch 40, which is connected to the console 10 by another cable 50. Thus, in use a surgeon may apply an ultrasonic electrical signal to the hand piece, causing the blade to vibrate longitudinally at an ultrasonic frequency, by operating the switch 34 on the hand piece with his finger, or by operating the foot switch 40 with his foot.

The generator console 10 includes a liquid crystal display device 12, which can be used for indicating the selected cutting power level in various means such as percentage of maximum cutting power or numerical power levels associated with cutting power. The liquid crystal display device 12 can also be utilized to display other parameters of the system. Power switch 11 is used to turn on the unit. While it is warming up, the "standby" light 13 is illuminated. When it is ready for operation, the "ready" indicator 14 is illuminated and the standby light goes out. If the unit is supplying maximum power, the MAX indicator is illuminated. If a lesser power is selected, the MIN indicator is illuminated. The level of power when MIN is active is set by button 16.

If a diagnostic test is to be performed, it is initiated by the "test" button 19. For safety reasons, e.g., to make sure a test is not started while the blade is touching the surgeon or other personnel, the button 19 may be depressed in combination with hand piece switch 34 or foot switch 40. Also, if the hand switch 34 is to be operative instead of foot switch 40, "hand activation" button 18 on the front panel must be selected or enabled using button 18.

When power is applied to the ultrasonic hand piece by operation of either switch 34 or 40, the assembly will cause the surgical scalpel or blade to vibrate longitudinally at approximately 55.5 kHz, and the amount of longitudinal movement will vary proportionately with the amount of driving power (current) applied, as adjustably selected by the user. When relatively high cutting power is applied, the blade is designed to move longitudinally in the range of about 40 to 100 microns at the ultrasonic vibrational rate. Such ultrasonic vibration of the blade will generate heat as the blade contacts tissue, i.e., the acceleration of the blade through the tissue converts the mechanical energy of the moving blade to thermal energy in a very narrow and localized area. This localized heat creates a narrow zone of coagulation, which will reduce or eliminate bleeding in small vessels, such as those less than one millimeter in diameter. The cutting efficiency of the blade, as well as the degree of hemostasis, will vary with the level of driving power applied, the cutting rate of the surgeon, the nature of the tissue type and the vascularity of the tissue.

As illustrated in more detail in FIG. 2, the ultrasonic hand piece 30 houses a piezoelectric transducer 36 for converting electrical energy to mechanical energy that results in longitudinal vibrational motion of the ends of the transducer. The transducer 36 is in the form of a stack of ceramic piezoelectric elements with a motion null point located at some point along the stack. The transducer stack is mounted between two cylinders 31 and 33. In addition a cylinder 35 is attached to cylinder 33, which is mounted to the housing at another motion null point 37. A horn 38 is also attached to the null point on one side and to a coupler 39 on the other side. Blade 32 is fixed to the coupler 39. As a result, the blade 32 will vibrate in the longitudinal direction at an ultrasonic frequency with the transducer 36. The ends of the transducer achieve maximum motion with a portion of the stack constituting a motionless node, when the transducer is driven with a maximum current at the transducers' resonant frequency. However, the current providing the maximum motion will vary with each hand piece and is a value stored in the non-volatile memory of the hand piece so the system can use it.

The parts of the hand piece are designed such that the combination will oscillate at the same resonant frequency. In particular, the elements are tuned such that the resulting length of each such element is one-half wavelength. Longitudinal back and forth motion is amplified as the diameter closer to the blade 32 of the acoustical mounting horn 38 decreases. Thus, the horn 38 as well as the blade/coupler are shaped and dimensioned so as to amplify blade motion and provide harmonic vibration in resonance with the rest of the acoustic system, which produces the maximum back and forth motion of the end of the acoustical mounting horn 38 close to the blade 32. A motion at the transducer stack is amplified by the horn 38 into a movement of about 20 to 25 microns. A motion at the coupler 39 is amplified by the blade 32 into a blade movement of about 40 to 100 microns.

Figure 3B:
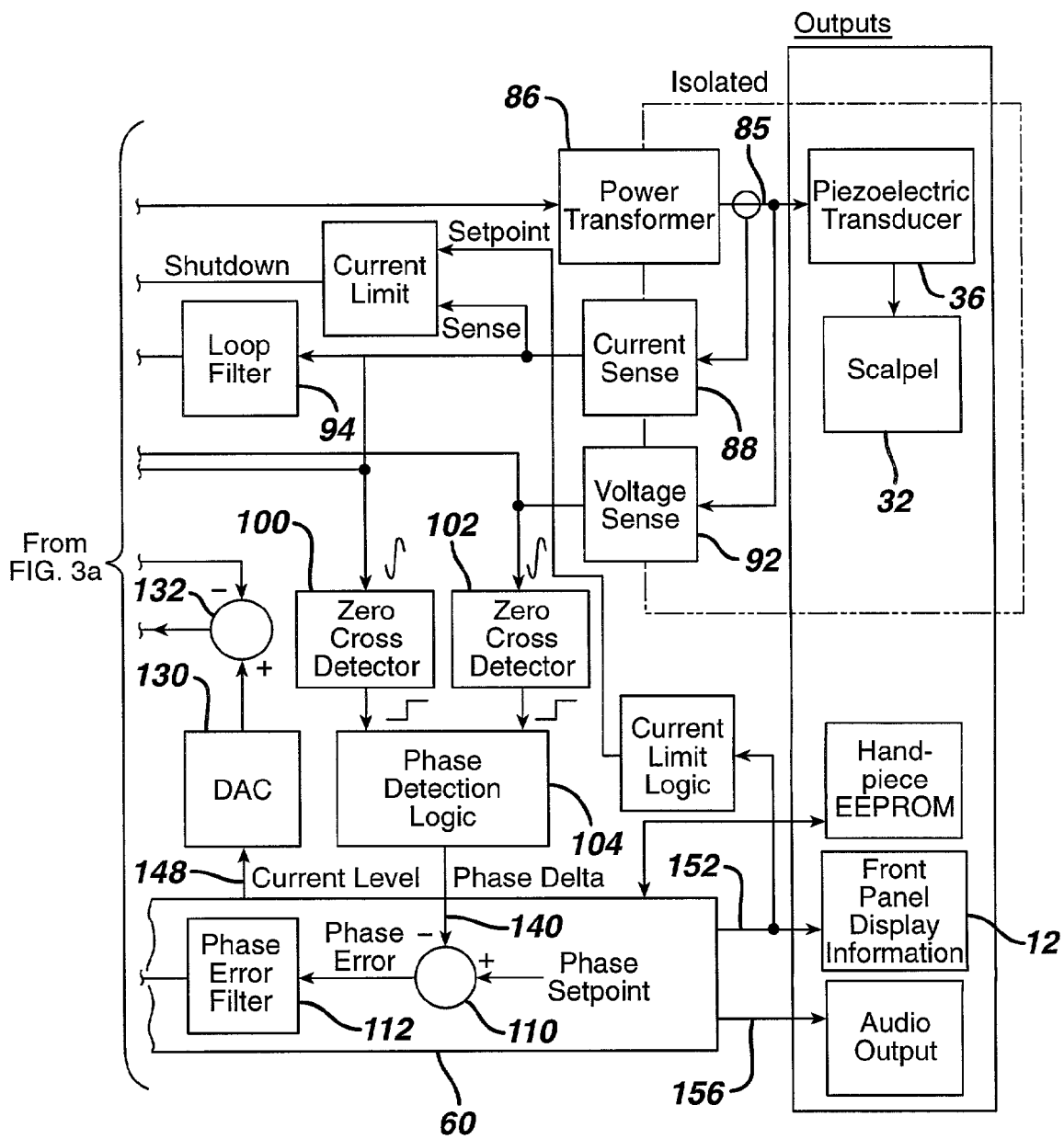

The system which creates the ultrasonic electrical signal for driving the transducer in the hand piece is illustrated in FIGS. 3(a) and 3(b). This drive system is flexible and can create a drive signal at a desired frequency and power level setting. A DSP 60 or microprocessor in the system is used for monitoring the appropriate power parameters and vibratory frequency as well as causing the appropriate power level to be provided in either the minimum or maximum operating modes. The DSP 60 or microprocessor also stores computer programs which are used to perform diagnostic tests on components of the system, such as the transducer/blade.

For example, under the control of a program stored in the DSP or microprocessor 60, such as a phase correction algorithm, the frequency during startup can be set to a particular value, e.g., 50 kHz. It can than be caused to sweep up at a particular rate until a change in impedance, indicating the approach to resonance, is detected. Then the sweep rate can be reduced so that the system does not overshoot the resonance frequency, e.g., 55 kHz. The sweep rate can be achieved by having the frequency change in increments, e.g., 50 cycles. If a slower rate is desired, the program can decrease the increment, e.g., to 25 cycles which both can be based adaptively on the measured transducer impedance magnitude and phase. Of course, a faster rate can be achieved by increasing the size of the increment. Further, the rate of sweep can be changed by changing the rate at which the frequency increment is updated.

If it is known that there is a undesired resonant mode, e.g., at say 51 kHz, the program can cause the frequency to sweep down, e.g., from 60 kHz, to find resonance. Also, the system can sweep up from 50 kHz and hop over 51 kHz where the undesired resonance is located. In any event, the system has a great degree of flexibility In operation, the user sets a particular power level to be used with the surgical instrument. This is done with power level selection switch 16 on the front panel of the console. The switch generates signals 150 that are applied to the DSP 60. The DSP 60 then displays the selected power level by sending a signal on line 152 (FIG. 3(b)) to the console front panel display 12. Further, the DSP or microprocessor 60 generates a digital current level signal 148 that is converted to an analog signal by digital-to-analog converter (DAC) 130. A signal representing the average output current from circuit 120 is applied to the negative input of node 132. The output of node 132 is a current error signal or amplitude control signal which is applied to direct digital synthesis (DDS) circuit 128 to adjust the amplitude of its output, as opposed to the frequency of its output, which is controlled by the signal on line 146 from the DSP or microprocessor 60. The arrangement of current level signal 148, DAC 130, summing node 130, and signal supplied by average output voltage 122 allows the DSP or microprocessor 60 to adjust the output current such that it can generate a desired power versus load curve when not in constant current mode.

To actually cause the surgical blade to vibrate, the user activates the foot switch 40 or the hand piece switch 34. This activation puts a signal on line 154 in FIG. 3(*a*). This signal is effective to cause power to be delivered from push-pull amplifier 78 to the transducer 36. When the DSP or microprocessor 60 has achieved lock on the hand piece transducer resonance frequency and power has been successfully applied to the hand piece transducer, an audio drive signal is put on line 156. This causes an audio indication in the system to sound, which communicates to the user that power is being delivered to the hand piece and that the scalpel is active and operational.

Figure 4:
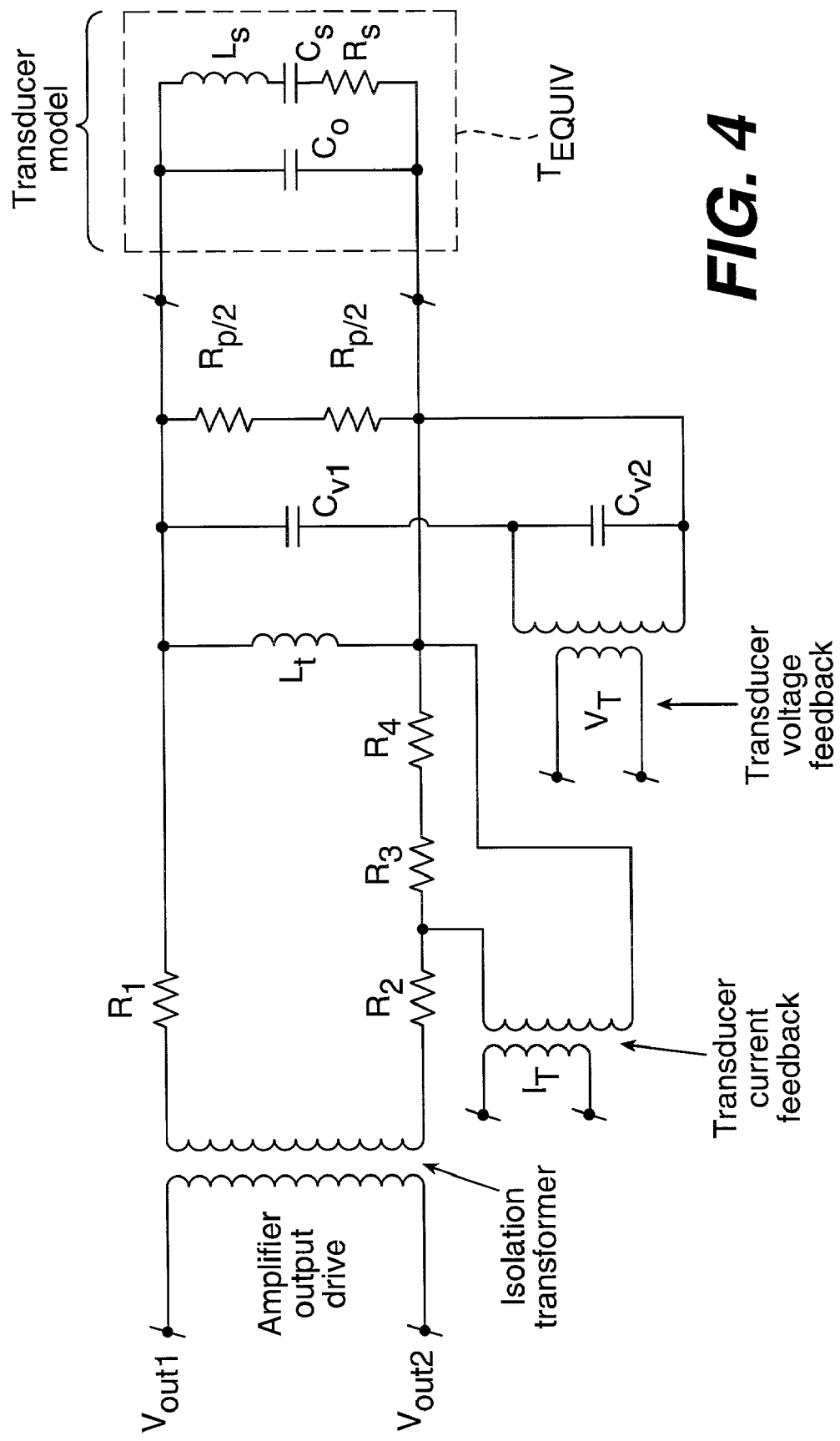
FIG. 4 is a schematic illustration of transducer drive circuitry of a power transformer of FIG. 3(b).

FIG. 4 is a schematic illustration of transducer drive circuitry of a power transformer of FIG. 3(*b*). The transducer is represented by an equivalent electrical circuit with The components $C_0$, $L_s$, $C_s$, and $R_s$ form a transducer equivalent circuit $T_{equiv}$, where $C_0$ is a shunt capacitance and represents the electrical capacitance of the piezoelectric elements of the piezoelectric transducer 36 shown in FIG. 2.

$L_s$, $C_s$ and $R_s$ are an electrical equivalent of the overall mechanical system and collectively represent the mechanical branch. $L_s$ is the effective mass of the system, $C_s$ is the effective compliance and $R_s$ represents mechanical losses associated with friction, internal material dissipation and/or the power delivered to the tissue.

Inductor $L_t$ is matched to the shunt capacitance $C_0$ at the resonance of the ultrasonic system, such as approximately 55.5 kHz. Hence, $L_t$ and $C_0$ electrically cancel each other at the resonant frequency. As a result, all of the drive current will flow through the mechanical branch. This helps to ensure that the ultrasonic excursion of the transducer is primarily proportional to the drive current.

The two resistors $R_p/2$ sum in series to a resistance of $R_p$. This resistance helps to establish an upper limit of the overall impedance of the output circuit, and also establishes an upper limit for the drive voltage. In preferred embodiments, $R_p$ is a relatively large resistance. At resonance, the parallel combination of $R_p$ and $R_s$ is effectively $R_s$, because $R_s$ is much smaller then $R_p$, even when coagulating and cutting tissue.

The series combination of capacitors $C_{v1}$ and $C_{v2}$ forms a voltage divider. Together these capacitors reduce the high voltage that typically drives the transducer to a level which is appropriate for signal processing by integrated circuits (not shown). A transformer $V_t$ couples the reduced voltage to the feedback circuitry (voltage sense 92 of FIG. 3(*b*)) and also provides isolation between the drive circuitry and the other circuitry of the generator.

A small voltage drop is provided across the series combination of resistors $R_3$ and $R_4$. In the preferred embodiment, the series combination is a relatively low resistance in the order of ohms. The voltage drop across $R_3$ and $R_4$ is proportional to the drive current. This voltage is provided to the feedback circuitry (current sense 88 of FIG. 3(*b*)) through a transformer $I_T$, which also isolates the drive circuitry from the rest of the circuitry of the generator. This signal represents current in the control algorithms implemented in the generator.

$R_1$ and $R_2$ are used to establish a minimum impedance level to the control circuitry for use in the control algorithms. The resistance is divided between the two output arms $V_{out1}$, $V_{out2}$ of the power transformer to help mitigate electromagnetic radiation and leakage current.

Figure 5:
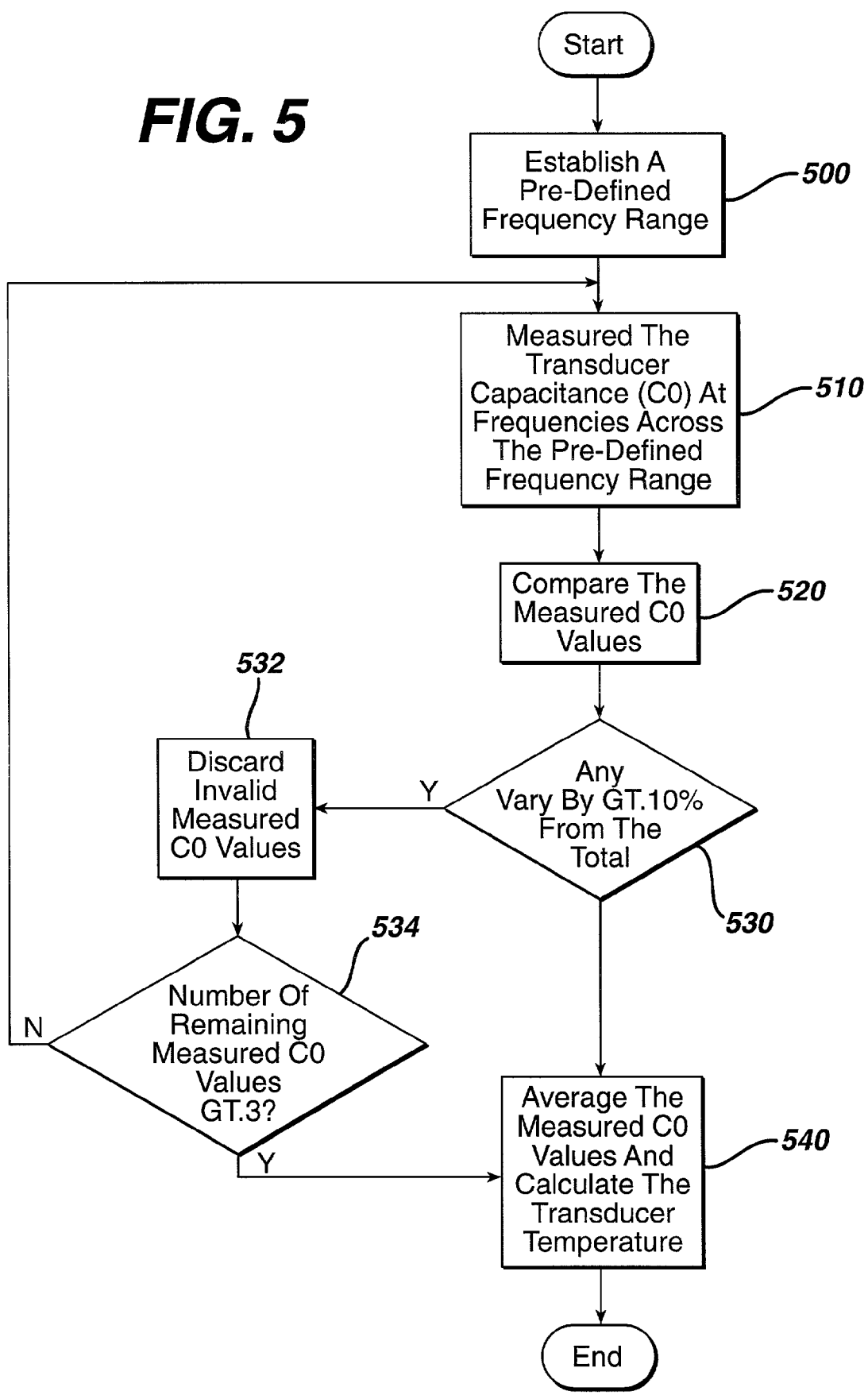
FIG. 5 is a flow chart illustrating an embodiment of the method of the invention.

FIG. 5 is a flow chart illustrating an embodiment of the method of the invention. Under control of the program stored in the DSP or microprocessor 60 shown in FIGS. 3(*a*) and 3(*b*), the method of the invention is implemented by applying an ultrasonic signal to the transducer 36 to drive the transducer/blade across a pre-defined frequency range, such as from 34 kHz to 36 kHz, as indicated in step 500. The pre-defined frequency range is set such that it will contain non-resonant frequencies where $C_0$ can be measured, and is set independently of a specific transducer/blade combination. The determination of the resonance frequency is not made during the initial attempt to measure $C_0$. Instead, $C_0$ is measured at several different frequencies (preferably at least 5 frequencies) within and spaced along the pre-defined frequency range, as indicated in step 510.

Next, the measured $C_0$ values are compared, as indicated in step 520. In step 530, a determination is made whether any of the measured $C_0$ values vary from each other by more than 10 percent. $C_0$ values which substantially vary from a majority of the measured $C_0$ values are deemed invalid and disregarded, and $C_0$ values which pass this test are deemed valid, as indicated in step 532. This "filtering" helps to eliminate invalid $C_0$ values, such as $C_0$ values which have been adversely influenced by a resonance or nearby resonance.

Next, a determination is made whether there are enough remaining valid $C_0$ values to ensure statistical validity, as indicated in step 534. In the preferred embodiment, the number of remaining values is at least 3. If an insufficient number of remaining valid $C_0$ values exists, a return to step 510 occurs. The method of the invention continues looping and measuring additional $C_0$ values until enough remaining valid $C_0$ are measured to ensure statistical validity. Once a statistically valid set of $C_0$ values is obtained, the valid $C_0$ values are averaged to obtain a derived $C_0$ value for the transducer which is used to determine whether the actual temperature of the transducer is excessive, as indicated in step 540.

To determine whether the transducer temperature is within acceptable limits, a calculation is performed in accordance with the relationship:

$$\Delta C_0 = C_s - C_0, \qquad \text{Eq. 1}$$

where $C_s$ is the capacitance at an off-resonance frequency which is stored in non-volatile memory located in the hand piece at room temperature.

Figure 8A:
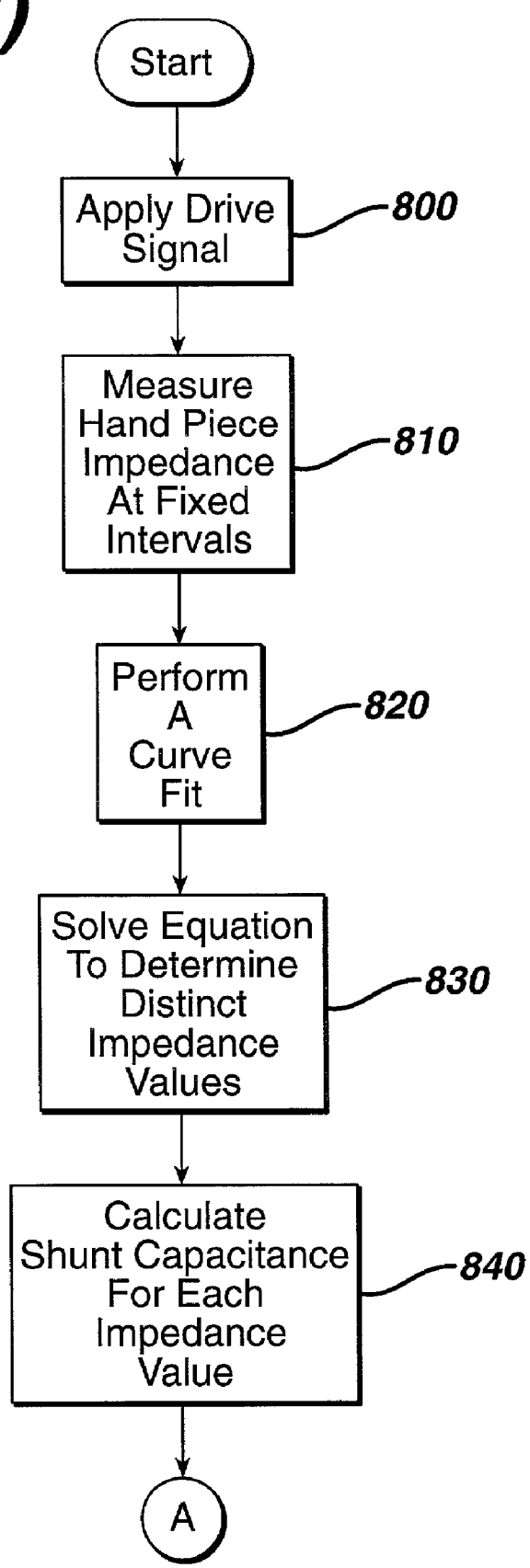
FIGS. 8(a) and 8(b) are flow charts illustrating a preferred embodiment of the method of the invention.
Figure 8B:
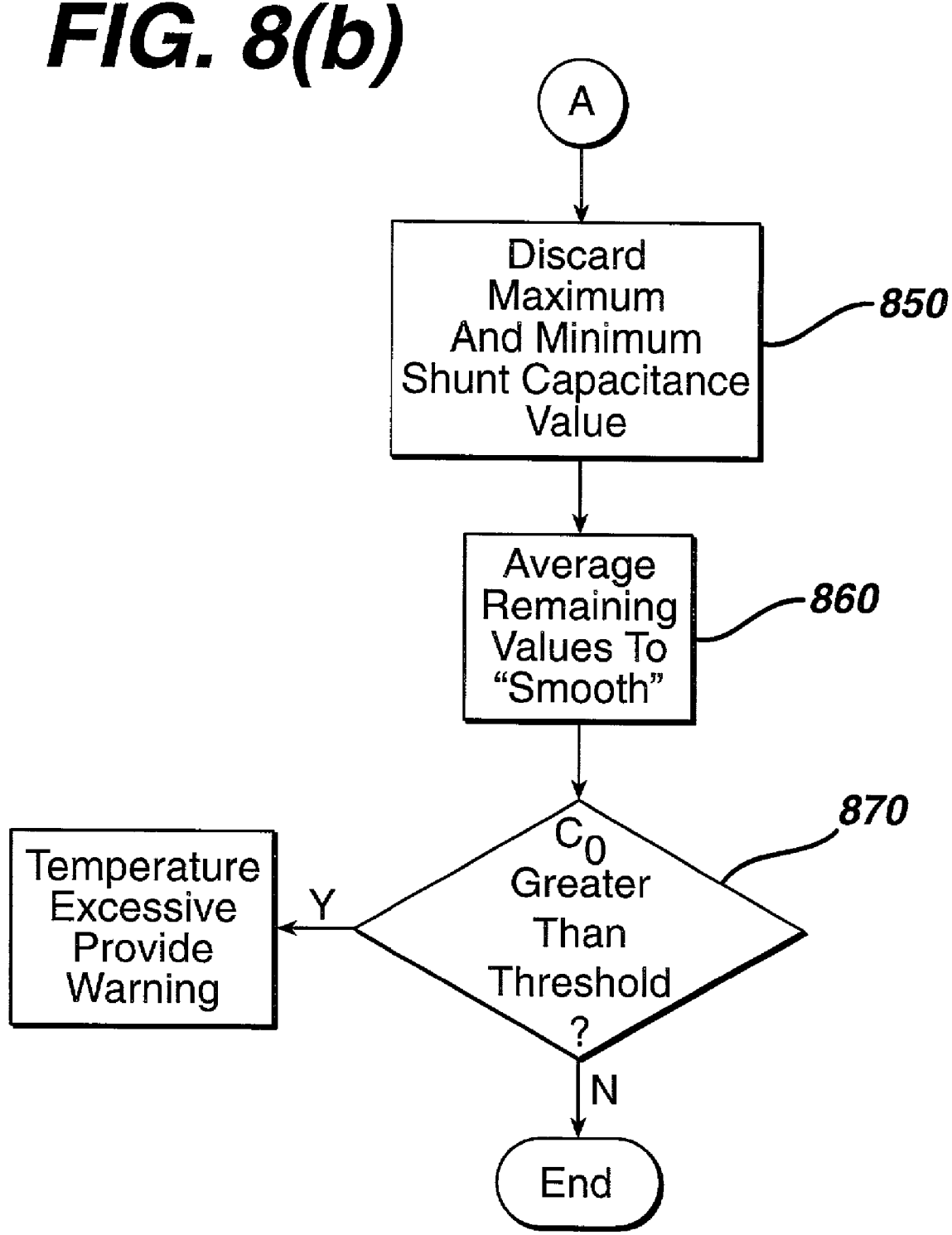

If $\Delta C_0$ is greater than a predetermined threshold based on the $C_0$/Temp relationship shown in FIG. 8, then the transducer temperature is excessive and a warning is provided to the user. Alternatively, power to the hand piece is removed until such time as the shunt capacitance falls below the predetermined threshold. In the preferred embodiment, the predetermined threshold is a fixed amount above the capacitance of the hand piece/blade at room temperature, and the fixed amount is 462 pF.

Figure 6:
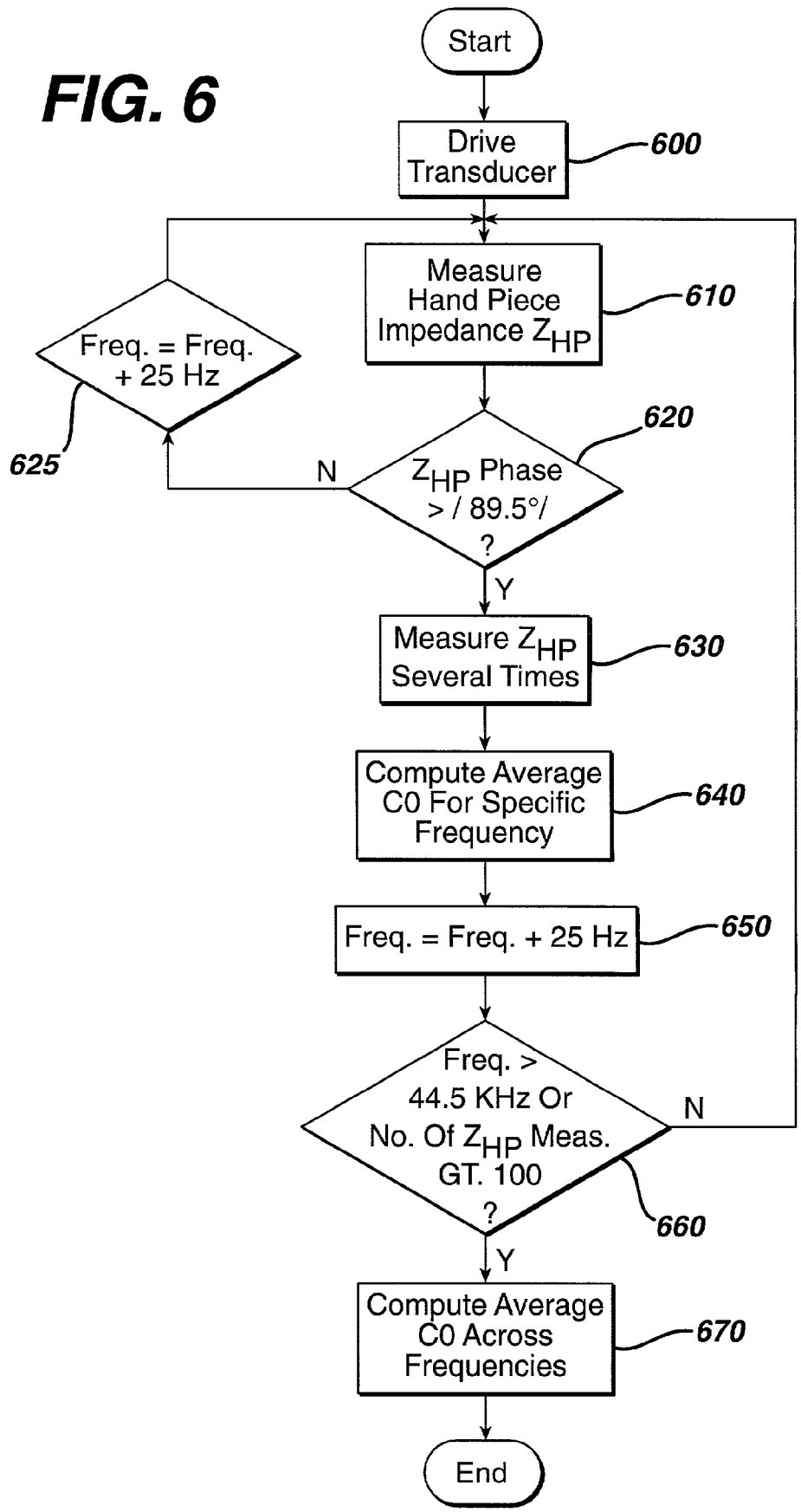
FIG. 6 is a flow chart illustrating another embodiment of the method of the invention.

FIG. 6 is a flow chart illustrating another embodiment of the method of the invention. During manufacture of the hand piece, the measured capacitance at an off-resonance frequency at room temperature (i.e., $C_0$ at a frequency other than resonance) is stored in non-volatile memory located in the hand piece (i.e., in an integrated circuit memory inside the connector, cable or body of the hand piece). Under control of the program stored in the DSP or microprocessor

60 shown in FIGS. 3(*a*) and 3(*b*), the method is implemented by applying an ultrasonic signal to the transducer 36 to drive the transducer/blade across a pre-defined frequency range, such as from 34 kHz to 44 kHz, as indicated in step 600.

The hand piece is measured to determine its impedance $Z_{HP}$, as indicated in step 610. A comparison is made to determine whether the absolute value of the phase difference between the voltage and current of the hand piece drive signal is greater than 89.5°, as indicated in step 620. If the absolute value of the phase difference of the hand piece drive signal is less than 89.5°, then the drive frequency is incremented by 25 Hz, as indicated in step 625. If, on the other hand, the absolute value of the phase difference of the hand piece drive signal is less than 89.5°, then $Z_{HP}$ of the hand piece is measured a number of times, as indicated in step 630. In the preferred embodiment, the impedance is measured 10 times.

An average $C_0$ is computed at the drive frequency in accordance with the relationship:

$$C_0 = \frac{1}{2\pi f |Z_{HP}|}, \qquad \text{Eq. 2}$$

where f is the drive frequency of the generator.

The drive frequency is incremented by 25 Hz, as indicated in step 650. A check is made to determined whether the drive frequency is greater than 44.5 kHz or whether the number of $Z_{HP}$ measurements is greater than 100, as indicated in step 660. If the answer to either test is yes, then the average value of the $C_0$ values measured at each drive frequency is computed, as indicated in step 670. If the drive frequency is less than 44.5 kHz and the number of $Z_{HP}$ measurements is less than 100, a return to step 610 occurs.

To determine whether the transducer temperature is within acceptable limits, a calculation is performed in accordance with the relationship:

$$\Delta C_0 = C_s - C_0, \qquad \text{Eq. 3}$$

where $C_s$ is the capacitance at an off-resonance frequency at room temperature which is stored in non-volatile memory located in the hand piece.

If $\Delta C_0$ is greater than a predetermined threshold based on the $C_0$/Temp relationship shown in FIG. 8, then the transducer temperature is excessive and a warning is provided to the user. Alternatively, power to the hand piece is removed until such time as the shunt capacitance falls below the predetermined threshold. In the preferred embodiment, the predetermined threshold is a fixed amount above the capacitance of the hand piece/blade at room temperature, and the fixed amount is 462 pF.

Figure 7:
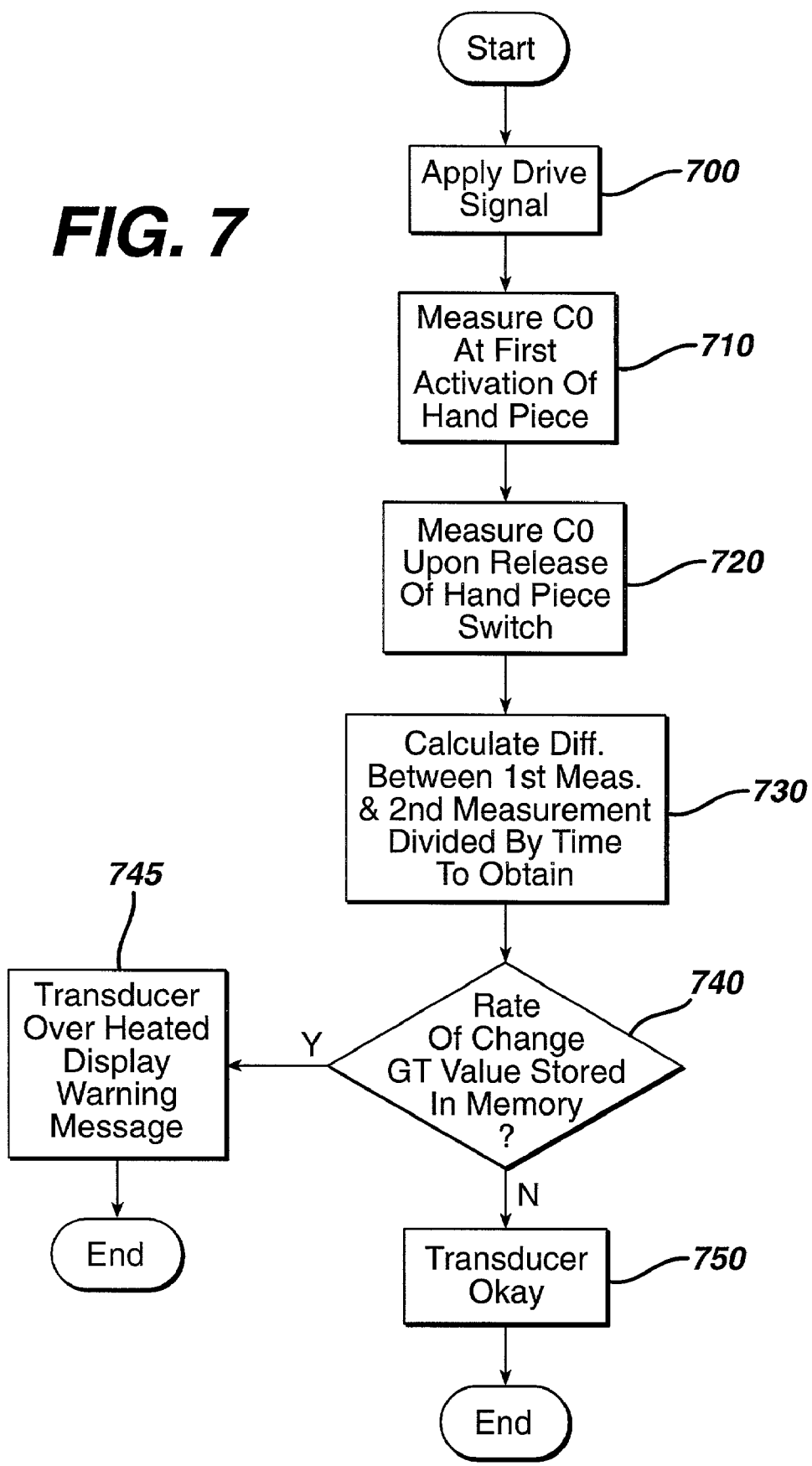
FIG. 7 is a flow chart illustrating another embodiment of the method of the invention.

FIG. 7 is a flow chart illustrating an alternative embodiment of the method of the invention. Here, the measured rate of change of the shunt capacitance ($C_0$) of the transducer is compared to a predetermined threshold above a $C_0$ rate of change value stored in non-volatile memory. During manufacture of the hand piece, the measured capacitance at an off-resonance frequency at room temperature is stored in non-volatile memory located in the hand piece. Under control of the program stored in the DSP or microprocessor 60 shown in FIGS. 3(*a*) and 3(*b*), the method is implemented by applying an ultrasonic signal to the transducer 36 to drive the transducer/blade across a pre-defined frequency range, such as from 34 kHz to 36 kHz, as indicated in step 700.

The $C_0$ of the transducer is first measured when a surgeon first activates the hand piece using the foot switch of the ultrasonic generator or the switch on the hand piece, as indicated in step 710. A second measurement is performed upon release of either switch by the surgeon, as indicated in step 720. Of note, no measurements are performed during actual use of the ultrasonic surgical system due to the time required to process each capacitance measurement.

Next, the difference between the first and second measurements is calculated and divided by the difference in time between when the first and second measurements were obtained to arrive at a value which is representative of the rate of change of the capacitance, as indicated in step 730.

A check is made to determine whether the rate of change value for the shunt capacitance exceeds the predetermined threshold above the $C_0$ rate of change value stored in the non-volatile memory, as indicated in 740. If the rate of change value for the shunt capacitance exceeds the predetermined threshold, a warning is provided to the surgeon before the temperature of the transducer becomes excessive, and therefore presents a danger of injury to the surgeon or patient, as indicated in step 745. On the other hand, if the rate of change is less than the predetermined value, the test is ended, as indicated in step 750. Of note, the rate of change value for the shunt capacitance is directly related to the rate of temperature rise of the transducer (see FIG. 8). In the preferred embodiment, the predetermined threshold is 120 pF/min.

FIGS. 8(*a*) and 8(*b*) are flow charts illustrating a preferred embodiment of the method of the invention. Under control of the program stored in the DSP or microprocessor 60 shown in FIGS. 3(*a*) and 3(*b*), the method is implemented by applying an ultrasonic signal to the transducer 36 to drive the transducer/blade across a pre-defined frequency range, such as from 34.5 kHz to 44.5 kHz, as indicated in step 800.

The hand piece is measured at fixed frequency intervals to determine its impedance $Z_{HP}$ at each frequency interval, as indicated in step 810. In the preferred embodiment, the fixed frequency interval is 50 Hz. Typically, resonances for known blades are not found in the pre-defined frequency range. However, $C_0$ can be influenced by resonances which are located slightly above or below the sweep range. Depending on whether the measurement is performed above or below the resonance frequency where $Z_{HP}$ is measured, resonances in the vicinity of the frequency tend to change the measured impedance value such that $C_0$ is shifted above or below the true $C_0$ value. The effect of these resonances is to cause errors in the measurement of the shunt capacitance ($C_0$) when discrete measurements are performed.

In accordance with the invention, this effect is mitigated by using data points obtained in step 810 to perform a curve fit, as indicated in step 820. In preferred embodiments, the curve fit is a least squares curve fit which is performed in accordance with the following relationship:

$$Z_{HP} = a f_0^2 + b f_0 + c, \qquad \text{Eq. 4}$$

where a, b and c are constants which are calculated via the curve fit and $f_0$ is a fixed frequency at which the hand piece impedance is measured.

The relationship in Eq. 4 is solved at a number of equally spaced frequency values to arrive at a group of distinct impedance values, as indicated in step 830. In the preferred embodiment, a total of eleven equally spaced frequencies across the sweep range (i.e., 34.5 kHz, 35.5 kHz . . . 44.5 kHz) are evaluated and the fixed frequency interval is 1000 Hz.

$C_0$ is calculated for each of the distinct impedance values, as indicated in step 840. In preferred embodiments, the calculation of $C_0$ is performed in accordance with the relationship:

$$C_0 = -(1/f_0)*(Z_{HP}^2 - 1/R_p^2)^{1/2} - (C_{v1}*C_{v2})/(C_{v1}°C_{v2}) + 1/(f_0^2*L_t) - C_c - C_{pcb},\quad \text{Eq. 5}$$

where $C_0$ is the shunt capacitance, $f_0$ is a fixed frequency at which the hand piece impedance is measured, $Z_{HP}$ is the calculated impedance at the fixed frequency $f_0$, $R_p$ is a value of a limiting resistor, $C_{v1}$ and $C_{v2}$ are values of voltage dividing capacitors, $L_t$ is a value stored in memory of the generator which represents a transducer tuning inductor, $C_{pcb}$ is the contribution of capacitance from a printed circuit board in the generator and $C_c$ is the capacitance of the hand piece cable.

The maximum calculated shunt capacitance value and the minimum calculated shunt capacitance value is discarded, as indicated in step 850. An average of the remaining values is then calculated to thereby "smooth" the high and low values, and arrive at a final shunt capacitance value, as indicated in step 860.

If $C_0$ is greater than a predetermined threshold based on the $C_0$/Temp relationship shown in FIG. 9, then the transducer temperature is excessive and a warning is provided to the user, as indicated in step 870. Alternatively, power to the hand piece is removed until such time as the shunt capacitance falls below the predetermined threshold. In the preferred embodiment, the predetermined threshold is a fixed amount above the capacitance of the hand piece/blade at room temperature, and the fixed amount is 462 pF.

By performing the curve fit, upward and downward fluctuations of the impedance measurements created by the resonances are "smoothed out" such that their effect (independent of their location relative to the sweep range) is significantly reduced. Calculating, discarding the high and low shunt capacitance values, and subsequently averaging the remaining shunt capacitance values further aids to "smooth" the data. As a result, measurement errors are also reduced.

Of note, if a resonance occurs in the middle of the sweep range, the curve fitting significantly reduces the influence of the resonances upon the measured shunt capacitance. In contemplated embodiments, linear (i.e., a first order equation) and quadratic curve (i.e., a second order equation) fits are used. However, any curve fit may be used provided that the equation smooths the data, as opposed to following it precisely. For instance, a curve fit which follows the measured data exactly is not beneficial, since no data smoothing would occur.

In another embodiment of the invention, during manufacture of the hand piece, the measured capacitance at an off-resonance frequency (i.e., the shunt capacitance ($C_0$) at a frequency other than resonance) is stored in non-volatile memory located in the hand piece (i.e., in an integrated circuit memory inside the connector, cable or body of the hand piece). Linear regression analysis of the values of the transducer capacitance, as it changes with temperature and hand piece use, is also stored in non-volatile memory located in the generator.

Prior to and/or during hand piece activation, the generator performs a "read" of the room temperature capacitance data from the hand piece. The actual capacitance of the hand piece is then measured in accordance with the invention, and the actual transducer temperature is calculated using a polynomial curve (see FIG. 8, for example) stored in the non-volatile memory of the generator.

The temperature data is then used to determined whether it is safe to activate the hand piece, as well as to determine what levels of parameters to expect during diagnostic measurements. It will be appreciated that the actual temperature measurement can be utilized for other purposes, such as to determine whether he hand piece operating at optimal conditions and to predict changes in the hand piece resonance frequency.

In alternative embodiments, the curve fitting is performed as a supplement to instances where the magnitude of the phased difference between the voltage and current applied to the hand piece/blade is used to filter the data prior to calculation of the shunt capacitance.

Using the method of the invention, the need to obtain prior knowledge of the transducer resonance is eliminated, and thus the speed at which $C_0$ is determined is greatly enhanced. By selectively averaging $C_0$ measurement obtained at different frequencies, a highly accurate $C_0$ measurement is obtained. Moreover, by eliminating $C_0$ measurements which appear disrupted by resonances and by focusing only on distinct potentially valid $C_0$ values, a faster calculation and identification of highly accurate $C_0$ values is achieved. As a result, an indicator of problems before the temperature of the hand piece becomes excessive is achieved.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. A method for determining temperature of a transducer of an ultrasonic hand piece, comprising the steps of:
    determining a shunt capacitance of the transducer comprising the steps of;
    applying an ultrasonic drive signal to the transducer across a pre-defined frequency range;
    measuring the hand piece impedance at fixed frequency intervals to obtain a measured impedance at each frequency interval;
    performing a curve fit based on each measured impedance at each frequency interval to obtain a curve fit equation;
    solving the curve fit equation at equally spaced frequency values to obtain a group of distinct impedance values;
    calculating a shunt capacitance based on each distinct impedance value;
    discarding a maximum and a minimum calculated shunt capacitance value to obtain a residual group of shunt capacitances; and
    averaging the residual group of shunt capacitances to obtain a final shunt capacitance value of the hand piece;
    calculating the temperature of the transducer based on the shunt capacitance of the transducer; and
    providing a warning to a user of the hand piece if one of the temperature of the transducer and a rate of change of the temperature is excessive.

2. The method of claim 1, wherein said determining step comprises the steps of:
    applying an ultrasonic drive signal to the hand piece/blade across a pre-defined frequency range;
    measuring a first hand piece shunt capacitance when a user first activates the hand piece/blade;

measuring a second hand piece/blade shunt capacitance when the surgeon deactivates the hand piece/blade;

calculating a time difference between when the hand piece/blade is activated and deactivated using a time when the first measured hand piece/blade shunt capacitance is obtained and a time when the second measured hand piece/blade shunt capacitance is obtained;

computing a rate of change value of the hand piece/blade shunt capacitance using the calculated time difference;

determining whether the rate of change value of the hand piece/blade shunt capacitance is greater than a predetermined threshold above a value stored in memory; and providing a warning to the user, if the rate of change value of the hand piece/blade shunt capacitance is greater than the predetermined threshold above the value stored in memory.

3. The method of claim 2, wherein the predefined frequency range is from approximately 34 kHz to 44 kHz.

4. The method of claim 2, wherein said computing step comprises the step of:

dividing a difference between the first measured hand piece/blade shunt capacitance and the second measured hand piece/blade shunt capacitance by a difference in time between when the first measured hand piece/blade shunt capacitance is obtained and when the second measured hand piece/blade shunt capacitance is obtained.

5. The method of claim 2, wherein the predetermined threshold is a shunt capacitance rate of change value stored in memory.

6. The method of claim 5, wherein the predetermined threshold is 120 pF/min.

7. The method of claim 1, wherein the curve fit is performed in accordance with the relationship:

$$C_0 = \frac{1}{2\pi f |Z_{HP}|},$$

where a, b and c are constants which are calculated via the curve fit and $f_0$ is a fixed frequency at which the hand piece impedance is measured.

8. The method of claim 1, wherein the pre-defined frequency range is from approximately 34.5 kHz to 44.5 kHz.

9. The method of claim 1, wherein the fixed frequency Interval is 50 Hz.

10. The method of claim 1, wherein the shunt capacitance is calculated in accordance with the relationship:

$$C_o = -\left(\frac{1}{f_o}\right) * \left(Z_{HP}^2 - \frac{1}{R_p^2}\right)^{\frac{1}{2}} - \frac{(C_{v1} * C_{v2})}{(C_{v1} + C_{v2})} + \frac{1}{(f_0^2 \neq L_t)} - C_c - C_{pcb},$$

where $C_0$ is the shunt capacitance, $f_0$ is a fixed frequency at which the hand piece impedance is measured, $Z_{HP}$ is the hand piece impedance at the fixed frequency $F_0$, $R_p$ is a value of a limiting resistor, $C_{v1}$ and $C_{v2}$ are values of voltage dividing capacitors, $L_t$ is a value stored in memory of the generator which represents a transducer tuning inductor, $C_c$ is a capacitance of a hand piece cable and $C_{pcb}$ is a contribution of capacitance from a printed circuit board in the generator.

11. The method of claim 1, wherein the group of distinct impedance values comprises eleven impedance values.

12. The method of claim 1, wherein the equally spaced frequency values are spaced apart at 1000 Hz intervals.

* * * * *